United States Patent
Inui et al.

(10) Patent No.: US 7,091,155 B2
(45) Date of Patent: Aug. 15, 2006

(54) CATALYST FOR ESTER PRODUCTION AND PROCESS FOR PRODUCING ESTER

(75) Inventors: Kanichiro Inui, Kimitsu (JP); Takayoshi Takahashi, Sagamihara (JP); Toru Kurabayashi, Ichihara (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 10/294,606

(22) Filed: Nov. 15, 2002

(65) Prior Publication Data

US 2004/0242917 A1    Dec. 2, 2004

Related U.S. Application Data

(63) Continuation of application No. 09/936,139, filed as application No. PCT/JP00/01397 on Mar. 8, 2000, now abandoned.

(30) Foreign Application Priority Data

Mar. 8, 1999 (JP) ................................ 11-060136
Sep. 17, 1999 (JP) ................................ 11-263282

(51) Int. Cl.
*B01J 23/06* (2006.01)
*C07C 69/52* (2006.01)
*C07C 69/02* (2006.01)

(52) U.S. Cl. ...................... 502/342; 502/346; 560/205; 560/231; 560/238; 560/239

(58) Field of Classification Search ................ 502/238, 502/242, 244, 307, 308, 342, 343, 346; 560/205, 560/231, 238, 239
See application file for complete search history.

(56) References Cited

U.S. PATENT DOCUMENTS 4,666,945 A * 5/1987 Osugi et al. ................. 518/713
5,302,569 A * 4/1994 Horn et al. .................. 502/342
5,892,102 A * 4/1999 Mikami et al. .............. 560/210

OTHER PUBLICATIONS

Tao, et al., "Characterization of Cu/Zn/Al/Zr Catalysts for Direct Synthesis of Ester from Alcohol" Chinese J. of Catalysis, 19(1), pp. 77-80, Jan. 1998.*

* cited by examiner

*Primary Examiner*—Steven Bos
(74) *Attorney, Agent, or Firm*—Oblon, Spivak, McClelland, Maier & Neustadt, P.C.

(57) ABSTRACT

A catalyst for ester production which comprises zirconium oxide, copper, and at least one oxide selected from the group consisting of zinc oxide, chromium oxide, aluminum oxide and silicon oxide, and is obtainable by reducing with hydrogen a catalyst precursor prepared by the reaction of a salt containing at least one of metals constituting the oxides, a zirconium salt and a copper salt with an alkali hydroxide; and a process for producing an ester which comprises bringing either an alcohol or an alcohol and an aldehyde into contact with this catalyst in a gas phase.

9 Claims, No Drawings

CATALYST FOR ESTER PRODUCTION AND PROCESS FOR PRODUCING ESTER

CROSS-REFERENCE TO RELATED APPLICATIONS

The present application is a continuation application of application Ser. No. 09/936,139 filed Sep. 10, 2001.

TECHNICAL FIELD

This invention relates to a new catalyst for ester production and a process for producing a lower ester by this catalyst.

BACKGROUND ART

Lower esters represented by ethyl acetate have been used in large quantities as paint solvents, extracting solvents, intermediates for chemical products and medicines, or the like, and are important materials in the chemical industry.

Such lower esters have conventionally been produced by dehydrating esterification from carboxylic acids and alcohols or condensation of aldehydes which is called Tishchenko reaction. In recent years, a process for the production of esters from carboxylic acids and olefins using a heteropolyacid catalyst has been reported (JP-A 5-65248, etc.) and noted as a new process for producing ethyl acetate.

In prior art processes for the production of ethyl acetate, however, plural raw materials such as acids and alcohols or acids and olefins have been used and thus the procurement of plural sources for the raw materials has been required, or otherwise, raw materials such as acetaldehyde, which are not easy to procure in a non-industrial area and difficult to handle, have been used and thus procuring, stockpiling and handling the raw materials have not been easy.

For the manufacture of esters having different carbon chain lengths, dehydrating esterification from the corresponding acids and alcohols has been effective means. However, there has been a problem of corrosion of an apparatus, etc., since acids are used as raw materials.

A process for producing ethyl acetate from ethyl alcohol by oxidative esterification using a palladium catalyst is reported in Kogyou Kagaku Zasshi, vol. 71, No. 9, pages 1517–1522, 1968. JP-A 9-29099 discloses a process for producing an ester from an alcohol and an aldehyde by a palladium-lead catalyst. In these reactions which consume oxygen, however, industrially useful hydrogen is not utilizable as by-product, although esters are produced.

DISCLOSURE OF THE INVENTION

An object of the invention is to solve the technical problems in the prior art as mentioned above, and to provide a new catalyst for ester production and a process for producing an ester from a lower alcohol, or a lower alcohol and a lower aldehyde.

We have zealously studied and found a process for producing an ester from an alcohol, or an ester from an alcohol and an aldehyde by dehydrogenation, using a catalyst prepared in a particular manner which contains copper and zirconium oxide as essential components, and further, at least one metal oxide selected from the group consisting of zinc oxide, chromium oxide, aluminum oxide and silicon oxide, thus leading to the completion of the present invention.

The catalysts for ester production according to the invention are defined in the following items (1) to (11).

(1) A catalyst for ester production which comprises zirconium oxide, copper and at least one oxide selected from the group consisting of zinc oxide, chromium oxide, aluminum oxide and silicon oxide, and is obtainable by reducing with hydrogen a catalyst precursor prepared by the reaction of a salt containing at least one of metals constituting the oxides, a zirconium salt and a copper salt with an alkali hydroxide.

(2) The catalyst for ester production as defined in item (1), which comprises not more than 5 moles of zinc oxide, not more than 5 moles of chromium oxide, not more than 5 moles of aluminum oxide, not more than 200 moles of silicon oxide and 0.05–5 moles of zirconium oxide, per mole of copper.

(3) The catalyst for ester production as defined in item (1), which comprises not more than 2 moles of zinc oxide, not more than 5 moles of aluminum oxide and 0.05–5 moles of zirconium oxide, per mole of copper.

(4) The catalyst for ester production as defined in item (1), which comprises not more than 5 moles of zinc oxide and 0.05–5 moles of zirconium oxide, per mole of copper.

(5) The catalyst for ester production as defined in item (1), which comprises not more than 5 moles of aluminum oxide and 0.05–5 moles of zirconium oxide, per mole of copper.

(6) A $Cu$—$ZnO$—$Al_2O_3$—$ZrO_2$ catalyst for ester production, which is obtainable by reducing with hydrogen a calcined form (a catalyst precursor) of a precipitate prepared from a mixed aqueous solution of copper nitrate, zinc nitrate, aluminum nitrate and zirconyl nitrate, and an alkali hydroxide.

(7) The catalyst for ester production as defined in item (6) wherein the mixed aqueous solution contains not more than 2 moles of zinc nitrate, not more than 10 moles of aluminum nitrate and 0.05–5 moles of zirconyl nitrate, per mole of copper nitrate.

(8) A $Cu$—$ZnO$—$ZrO_2$ catalyst for ester production which is obtainable by reducing with hydrogen a calcined form (a catalyst precursor) of a precipitate prepared from a mixed aqueous solution of copper nitrate, zinc nitrate and zirconyl nitrate, and an alkali hydroxide.

(9) The catalyst for ester production as defined in item (8) wherein the mixed aqueous solution contains not more than 5 moles of zinc nitrate and 0.05–5 moles of zirconyl nitrate, per mole of copper nitrate.

(10) A $Cu$—$Al_2O_3$—$ZrO_2$ catalyst for ester production, which is obtainable by reducing with hydrogen a calcined form (a catalyst precursor) of a precipitate prepared from a mixed aqueous solution of copper nitrate, aluminum nitrate and zirconyl nitrate, and an alkali hydroxide.

(11) The catalyst for ester production as defined in item (10) wherein the mixed aqueous solution contains not more than 10 moles of aluminum nitrate and 0.05–5 moles of zirconyl nitrate, per mole of copper nitrate.

The processes for the production of esters according to the present invention are defined in the following items (12)–(18).

(12) A process for producing an ester, characterized by bringing an alcohol into contact with a catalyst as defined in any one of items (1)–(11) in vapor phase, and dehydrogenating the alcohol to form an ester.

(13) The process for producing an ester as defined in item (12) wherein the alcohol is an alcohol having 1–4 carbon atoms.

(14) The process for producing an ester as defined in item (12) wherein ethyl acetate is produced from ethyl alcohol.

(15) A process for producing an ester, characterized by bringing an alcohol and an aldehyde into contact with a catalyst as defined in any one of items (1)–(11) in vapor phase to form an ester.

(16) The process for producing an ester as defined in item (15) wherein the alcohol and the aldehyde are an alcohol and an aldehyde each having 1–4 carbon atoms.

(17) The process for producing an ester as defined in item (15) wherein ethyl acetate is produced from ethyl alcohol and acetaldehyde.

(18) The process for producing an ester as defined in item (15) wherein butyl acetate is produced from butyl alcohol and acetaldehyde.

BEST MODE FOR CARRYING OUT THE INVENTION

The catalyst for ester production according to the present invention is characterized by comprising zirconium oxide, copper and at least one oxide selected from the group consisting of zinc oxide, chromium oxide, aluminum oxide and silicon oxide, and being obtainable by reducing with hydrogen a catalyst precursor prepared by the reaction of a salt containing at least one of metals constituting the oxides, a zirconium salt and a copper salt with an alkali hydroxide.

For instance, an aqueous solution of an alkali hydroxide is added to an aqueous solution of a nitrate of a metal contained in the catalyst to precipitate a catalyst precursor comprising a metal hydroxide. The catalyst precursor is washed with water, dried and baked, and then reduced with hydrogen at 120–500° C. for 1–48 hours, thus reducing copper oxide to prepare an active metallic copper/zirconium oxide/oxide catalyst.

The catalyst for ester production according to the invention contains metallic copper and zirconium oxide as essential ingredients, and further contains one or more oxides selected from the group consisting of zinc oxide, chromium oxide, aluminum oxide and silicon oxide.

The contents of the oxides and zirconium oxide are not more than 5 moles of zinc oxide, not more than 5 moles of chromium oxide, not more than 5 moles of aluminum oxide, not more than 200 moles of silicon oxide and 0.05–5 moles of zirconium oxide, per mole of copper.

There is no limitation on reaction apparatuses used in the manufacture of the catalyst for ester production according to the invention particularly. Preferably, a predetermined amount of a catalyst precursor is charged in the reaction apparatus used in the manufacture of esters, and reduced with hydrogen and activated to form a catalyst. The apparatus is then charged with an ester raw material. For instance, a predetermined amount of a catalyst precursor is charged into a vapor-circulating reaction apparatus and reduced with hydrogen to form an active catalyst layer within the apparatus for ester manufacture.

In the preparation of the precipitate comprising metal hydroxides by reaction of metal nitrates with alkali hydroxides, methods such as coprecipitation and impregnation are suitably applied, but not limited thereto.

The contents of copper or metal oxides in the Cu—ZnO—$Al_2O_3$—$ZrO_2$ catalyst of the present invention are preferably not more than 2 moles of zinc oxide, not more than 5 moles of aluminum oxide and 0.05–5 moles of zirconium oxide, per mole of copper, and more preferably 0.05–1 mole of zinc oxide, 0.1–1 mole of aluminum oxide and 0.1–1 mole of zirconium oxide, per mole of copper. The content outside the preferred range results in the lower selectivity to the intended ester.

This catalyst is prepared by reducing with hydrogen a calcined form (a catalyst precursor) of the precipitate prepared from a mixed aqueous solution of copper nitrate, zinc nitrate, aluminum nitrate and zirconyl nitrate, and an alkali hydroxide. The mixed aqueous solution contains preferably not more than 2 moles of zinc nitrate, not more than 10 moles of aluminum nitrate and 0.05–5 moles of zirconyl nitrate, and more preferably 0.05–1 mole of zinc nitrate, 0.2–2 moles of aluminum nitrate and 0.1–1 mole of zirconyl nitrate, per mole of copper nitrate.

The contents of copper or metal oxides in the Cu—ZnO—$ZrO_2$ catalyst of the present invention are preferably not more than 5 moles of zinc oxide and 0.05–5 moles of zirconium oxide, per mole of copper, and more preferably 0.1–1 mole of zinc oxide and 0.1–1 mole of zirconium oxide, per mole of copper. The content outside the preferred range results in the lower selectivity to the intended ester.

This catalyst is prepared by reducing with hydrogen a calcined form (a catalyst precursor) of the precipitate obtained from a mixed aqueous solution of copper nitrate, zinc nitrate and zirconyl nitrate, and an alkali hydroxide. The mixed aqueous solution contains preferably not more than 5 moles of zinc nitrate and 0.05–5 moles of zirconyl nitrate, and more preferably 0.1–1 mole of zinc nitrate and 0.1–1 mole of zirconyl nitrate, per mole of copper nitrate.

The contents of copper or metal oxides in the Cu—$Al_2O_3$—$ZrO_2$ catalyst of the present invention are preferably not more than 5 moles of aluminum oxide and 0.05–5 moles of zirconium oxide, per mole of copper, and more preferably 0.1–1 mole of aluminum oxide and 0.1–1 mole of zirconium oxide, per mole of copper. The content outside the preferred range results in the lower selectivity to the intended ester.

This catalyst is prepared by reducing with hydrogen a calcined form (a catalyst precursor) of the precipitate obtained from a mixed aqueous solution of copper nitrate, aluminum nitrate and zirconyl nitrate, and an alkali hydroxide. The mixed aqueous solution contains preferably not more than 10 moles of aluminum nitrate and 0.05–5 moles of zirconyl nitrate, and more preferably 0.1–1 mole of aluminum nitrate and 0.1–1 mole of zirconyl nitrate, per mole of copper nitrate.

The process for the production of esters according to the present invention is characterized by bringing either an alcohol or an alcohol and an aldehyde into contact with the catalyst of the present invention in vapor phase and subjecting to dehydrogenation to prepare an ester.

According to the present invention, preferable catalysts for ester production used in the processes for the production of esters are metallic copper/zirconium oxide/metal oxides, which are specifically Cu—ZnO—$Al_2O_3$—$ZrO_2$—$SiO_2$, Cu—ZnO—$Al_2O_3$—$ZrO_2$, Cu—ZnO—$ZrO_2$, Cu—$ZrO_2$, Cu—$Cr_2O_3$—$ZrO_2$ or the like.

For the manufacture of ethyl acetate from alcohol, the manufacture of ethyl acetate from alcohol and acetaldehyde, or the like, preferable are Cu—ZnO—$Al_2O_3$—$ZrO_2$—$SiO_2$, Cu—ZnO—$Al_2O_3$—$ZrO_2$, Cu—ZnO—$ZrO_2$, Cu—$ZrO_2$, Cu—$Cr_2O_3$—$ZrO_2$ or the like.

Alcohols for a raw material are preferably methyl alcohol, ethyl alcohol, propyl alcohol, isopropyl alcohol, butyl alcohol or the like. Aldehydes are preferably acetaldehyde, propionaldehyde, isobutylaldehyde, butylaldehyde or the like.

Esters produced from these raw materials include methyl formate, ethyl acetate, propyl propionate, butyl butyrate, n-butyl acetate and n-propyl acetate.

In particular, the present process for the production of esters is used preferably for the manufacture of ethyl acetate from ethyl alcohol and the manufacture of ethyl acetate from ethyl alcohol and acetaldehyde.

The reaction temperature in the process for the production of esters is suitably in the range of from 150 to 400° C. That is, it is the temperature at which an alcohol and an aldehyde exist in vapor phase. The reaction may insufficiently progress at lower than 150° C., while the selectivity to the product may lower at higher than 400° C.

The water content in alcohols and aldehydes as the raw materials is allowable in the range of 0–30% by weight, and it is preferably in the range of 0–15% by weight.

EXAMPLES

The effect of the present invention is concretely illustrated by the following Examples and Comparative Examples, to which the invention is not limited.

A normal-pressure vapor-circulating fixed-bed reaction apparatus used in the Examples and Comparative Examples is a reactor having a inner diameter of 17 mm and a total length of 600 mm (the upper part 400 mm in length is a vaporization layer packed with ceramic rings and the lower part is a catalyst layer 100 mm in length), equipped with a carrier gas introducing inlet and a raw material flowing inlet at the top end, and at the bottom end a vessel (cooled) for collecting a crude reaction solution which has a gas vent.

The crude reaction solution collected in the collecting vessel was determined by gas chromatography. After calibration correction and water content correction, the yield of ethyl acetate, etc. and the residual amount of raw materials such as ethyl alcohol were determined. From these values, conversion (% by weight), selectivity (% by weight) and yield (% by weight) were calculated.

Example 1

(Preparation of Catalyst)

In a flask, 97 g of copper nitrate, 40 g of zinc nitrate, 504 g of aluminum nitrate and 36 g of zirconyl nitrate were dissolved in 5 liters of water. To this solution was added an aqueous solution of 227 g of sodium hydroxide dissolved in 1 liter of water to prepare a precipitate. The precipitate (prepared by a so-called coprecipitation method) was washed with water, dried and baked to form a catalyst precursor.

In the normal-pressure vapor-circulating fixed-bed reaction apparatus, 15 g of the catalyst precursor were charged in the catalyst layer (17 mm in inner diameter, about 100 mm in length) and then reduced with a nitrogen-diluted hydrogen as a reducing agent at 200° C. or lower for 4 hours, and a Cu—ZnO—$Al_2O_3$—$ZrO_2$ catalyst layer for ester production was provided within this reaction apparatus.

(Production of Ester)

A nitrogen gas was flowed as a carrier gas at a constant rate of 20 ml/min from the top of the reaction apparatus provided with the Cu—ZnO—$Al_2O_3$—$ZrO_2$ catalyst layer. Together with this nitrogen gas, 99.5% by weight of ethyl alcohol were supplied, and ethyl alcohol was vaporized in the vaporization layer and fed to the catalyst layer to carry out the reaction. The temperatures in the vaporization and catalyst layers were 260° C.

Conversion of ethanol, selectivity to ethyl acetate and yield of ethyl acetate at respective LHSV's (Liquid Hourly Space Velocity) of ethanol are shown in the following table.

TABLE 1

| LHSV ($h^{-1}$) | Conversion of ethanol (%) | Selectivity to ethyl acetate (%) | Yield of ethyl acetate (%) |
| --- | --- | --- | --- |
| 0.2 | 82.4 | 71.5 | 58.9 |
| 0.5 | 67.0 | 61.0 | 40.9 |

Example 2

(Preparation of Catalyst)

In 5 liters of water were dissolved 97 g of copper nitrate, 40 g of zinc nitrate and 36 g of zirconyl nitrate. To this solution was added an aqueous solution of 64 g of sodium hydroxide dissolved in 1 liter of water to prepare a precipitate. The precipitate (prepared by a so-called coprecipitation method) was washed with water, dried and baked to form a catalyst precursor.

In accordance with the procedure of Example 1, a Cu—ZnO—$ZrO_2$ catalyst layer for ester production was provided in the normal-pressure vapor-circulating fixed-bed reaction apparatus.

(Production of Ester)

Ethyl acetate was produced by performing the reaction in accordance with the procedure of Example 1, except for using the fixed-bed reaction apparatus provided with the Cu—ZnO—$ZrO_2$ catalyst layer and 99% ethyl alcohol. The result of the reaction is shown in the following table.

TABLE 2

| LHSV ($h^{-1}$) | Conversion of ethanol (%) | Selectivity to ethyl acetate (%) | Yield of ethyl acetate (%) |
| --- | --- | --- | --- |
| 0.5 | 86.0 | 62.0 | 53.3 |
| 1.0 | 80.5 | 60.5 | 48.7 |

Example 3

The reaction was performed under the same condition as in Example 2, except for using 95% ethanol as a reaction material. The result is shown in the following table.

TABLE 3

| LHSV ($h^{-1}$) | Conversion of ethanol (%) | Selectivity to ethyl acetate (%) | Yield of ethyl acetate (%) |
| --- | --- | --- | --- |
| 0.2 | 67.9 | 57.5 | 39.0 |

Example 4

The reaction was performed under the same condition as in Example 2, except that the reaction temperature was 300° C. The result is shown in the following table.

TABLE 4

| LHSV (h$^{-1}$) | Conversion of ethanol (%) | Selectivity to ethyl acetate (%) | Yield of ethyl acetate (%) |
|---|---|---|---|
| 0.2 | 80.2 | 49.2 | 39.5 |

Example 5

The reaction was performed under the same condition as in Example 2, except for using n-butanol and acetaldehyde (mole ratio of n-butanol:acetaldehyde=80:20) as a raw material. The result is shown in the following table.

TABLE 5

| LHSV (h$^{-1}$) | Conversion of n-butanol (%) | Selectivity to n-butyl acetate (%) | Yield of n-butyl acetate (%) |
|---|---|---|---|
| 0.2 | 69.3 | 14.5 | 10.0 |

Example 6

The reaction was performed under the same condition as in Example 2, except for using n-butanol as a raw material. The result is shown in the following table.

TABLE 6

| LHSV (h$^{-1}$) | Conversion of n-butanol (%) | Selectivity to butyl butyrate (%) | Yield of butyl butyrate (%) |
|---|---|---|---|
| 0.2 | 69.0 | 46.2 | 31.9 |

Example 7

(Preparation of Catalyst)

In a flask, 156 g of copper nitrate, 162 g of aluminum nitrate and 58 g of zirconyl nitrate were dissolved in 5 liters of water. To this solution was added an aqueous solution of 191 g of sodium hydroxide dissolved in 1 liter of water. The resulting precipitate was washed with water, dried and baked to form a catalyst precursor.

In the normal-pressure vapor-circulating fixed-bed reaction apparatus, 15 g of the catalyst precursor were charged in the catalyst layer (17 mm in inner diameter, about 100 mm in length) and then reduced with a nitrogen-diluted hydrogen as a reducing agent at 200° C. or lower for 4 hours, and a Cu—Al$_2$O$_3$—ZrO$_2$ catalyst layer for ester production was provided within the reaction apparatus.

(Production of Ester)

Ethyl alcohol (99.5%) as a raw material and nitrogen as a carrier gas were supplied from the top of the fixed-bed reaction apparatus provided with the Cu—Al$_2$O$_3$—ZrO$_2$ catalyst layer, thereby initiating a reaction. Ethyl alcohol was vaporized in the vaporization layer and fed to the catalyst layer. The amount of nitrogen supplied as a carrier gas was 20 ml/min. The temperatures in the vaporization and catalyst layers are shown in the table as the reaction temperature.

Conversion of ethanol, selectivity to ethyl acetate and yield of ethyl acetate at respective LHSV's (Liquid Hourly Space Velocity) of ethanol are shown in the following table.

TABLE 7

| LHSV (h$^{-1}$) | Reaction temperature (° C.) | Conversion of ethanol (%) | Selectivity to ethyl acetate (%) | Yield of ethyl acetate (%) |
|---|---|---|---|---|
| 0.5 | 280 | 88.5 | 56.6 | 50.1 |
|  | 260 | 86.3 | 70.5 | 60.8 |
|  | 240 | 79.3 | 78.1 | 61.9 |
| 0.2 | 260 | 88.7 | 58.7 | 52.1 |
| 0.5 |  | 86.3 | 70.5 | 60.8 |
| 1.0 |  | 83.7 | 69.9 | 58.5 |

Example 8

(Preparation of Catalyst)

In a flask, 195 g of copper nitrate, 20 g of zinc nitrate, 101 g of aluminum nitrate and 36 g of zirconyl nitrate were dissolved in 5 liters of water. To this solution was added an aqueous solution of 179 g of sodium hydroxide dissolved in 1 liter of water. The resulting precipitate was washed with water, dried and baked to form a catalyst precursor.

In a similar manner as in Example 7, 15 g of the catalyst precursor were treated and a Cu—ZnO—ZrO$_2$ catalyst layer for ester production was provided within the normal-pressure vapor-circulating fixed-bed reaction apparatus.

(Production of Ester)

Ethyl acetate was produced by performing the reaction in accordance with the procedure of Example 7, except for using the fixed-bed reaction apparatus provided with the Cu—ZnO—ZrO$_2$ catalyst layer.

The results at respective LHSV's of ethanol are shown in the following table.

TABLE 8

| LHSV (h$^{-1}$) | Reaction temperature (° C.) | Conversion of ethanol (%) | Selectivity to ethyl acetate (%) | Yield of ethyl acetate (%) |
|---|---|---|---|---|
| 0.5 | 280 | 88.0 | 62.1 | 54.7 |
|  | 260 | 85.9 | 74.8 | 64.2 |
|  | 240 | 78.6 | 80.2 | 63.1 |
|  | 220 | 66.4 | 83.8 | 55.6 |
| 0.2 | 260 | 88.5 | 59.8 | 52.9 |
| 0.5 |  | 85.9 | 74.8 | 64.2 |
| 1.0 |  | 82.5 | 74.7 | 61.6 |

Example 9

(Preparation of Catalyst)

In a flask, 209 g of copper nitrate, 21 g of zinc nitrate, 54 g of aluminum nitrate and 39 g of zirconyl nitrate were dissolved in 5 liters of water. To this solution was added an aqueous solution of 165 g of sodium hydroxide dissolved in 1 liter of water. The resulting precipitate was washed with water, dried and baked to form a catalyst precursor.

In a similar manner as in Example 7, 15 g of the catalyst precursor were treated and a Cu—ZnO—Al$_2$O$_3$ catalyst layer for ester production was provided within the normal-pressure vapor-circulating fixed-bed reaction apparatus.

(Production of Ester)

Ethyl acetate was produced by performing the reaction in accordance with the procedure of Example 7, except for using the fixed-bed reaction apparatus provided with the Cu—ZnO—Al$_2$O$_3$ catalyst layer.

The results at respective LHSV's of ethanol are shown in the following table.

TABLE 9

| LHSV (h$^{-1}$) | Reaction temperature (° C.) | Conversion of ethanol (%) | Selectivity to ethyl acetate (%) | Yield of ethyl acetate (%) |
|---|---|---|---|---|
| 0.5 | 280 | 87.6 | 65.2 | 57.1 |
|  | 260 | 84.2 | 78.8 | 66.3 |
|  | 240 | 74.4 | 83.6 | 62.2 |
|  | 220 | 55.0 | 83.2 | 45.7 |
| 1.0 | 240 | 59.1 | 75.2 | 44.4 |
|  | 260 | 80.3 | 78.6 | 63.1 |
|  | 280 | 85.0 | 70.7 | 60.1 |

Example 10

(Preparation of Catalyst)

In a flask, 213 g of copper nitrate, 22 g of zinc nitrate, 110 g of aluminum nitrate and 20 g of zirconyl nitrate were dissolved in 5 liters of water. To this solution was added an aqueous solution of 186 g of sodium hydroxide dissolved in 1 liter of water. The resulting precipitate was washed with water, dried and baked to form a catalyst precursor.

In a similar manner as in Example 7, 15 g of the catalyst precursor were treated and a Cu—ZnO—Al$_2$O$_3$ catalyst layer for ester production was provided within the normal-pressure vapor-circulating fixed-bed reaction apparatus.

(Production of Ester)

Ethyl acetate was produced by performing the reaction in accordance with the procedure of Example 7, except for using the fixed-bed reaction apparatus provided with the Cu—ZnO—Al$_2$O$_3$ catalyst layer.

The results at respective LHSV's of ethanol are shown in the following table.

TABLE 10

| LHSV (h$^{-1}$) | Reaction temperature (° C.) | Conversion of ethanol (%) | Selectivity to ethyl acetate (%) | Yield of ethyl acetate (%) |
|---|---|---|---|---|
| 0.5 | 280 | 89.9 | 56.8 | 51.1 |
|  | 260 | 87.4 | 73.0 | 62.9 |
|  | 240 | 81.0 | 77.5 | 62.8 |
| 0.2 | 260 | 89.8 | 62.7 | 56.3 |
| 0.5 |  | 87.4 | 73.0 | 62.9 |
| 1.0 |  | 79.0 | 69.7 | 55.0 |

Comparative Example 1

(Preparation of Catalyst)

48 g of copper oxide, 16 g of zinc oxide, 102 g of aluminum oxide and 25 g of zirconium oxide were physically mixed with 150 g of water, and the mixture was dried and baked at 200° C. to prepare a grayish white solid catalyst precursor.

In accordance with the procedure of Example 1, a Cu—ZnO—Al$_2$O$_3$—ZrO$_2$ catalyst layer for ester production was provided within the normal-pressure vapor-circulating fixed-bed reaction apparatus.

(Production of Ester)

A nitrogen gas was flowed as a carrier gas at a constant rate of 20 ml/min from the top of the fixed-bed reaction apparatus provided with the catalyst layer for ester production. Together with this nitrogen gas, 99.5% by weight of ethyl alcohol were supplied, ethyl alcohol was vaporized in the vaporization layer packed with ceramic rings which was provided at the top of the catalyst layer, and fed to the catalyst layer to carry out the reaction. The temperatures in the vaporization and catalyst layers were 260° C. The result of the reaction is shown in the following table.

TABLE 11

| LHSV (h$^{-1}$) | Conversion of ethanol (%) | Selectivity to ethyl acetate (%) | Yield of ethyl acetate (%) |
|---|---|---|---|
| 0.5 | 27.7 | 0.9 | 0.2 |
| 1.0 | 21.8 | 0.7 | 0.2 |

Comparative Example 2

The reaction was performed in a similar manner as in Example 1, except for replacing 227 g of sodium hydroxide by 540 ml of 30% aqueous ammonia. The result is shown in the following table.

TABLE 12

| LHSV (h$^{-1}$) | Conversion of ethanol (%) | Selectivity to ethyl acetate (%) | Yield of ethyl acetate (%) |
|---|---|---|---|
| 0.5 | 79.6 | 57.4 | 45.7 |

INDUSTRIAL APPLICABILITY

The catalyst of the present invention exhibits an excellent activity as a dehydrogenation catalyst, and makes it possible to produce esters in high yield and high selectivity from alcohols, or from alcohols and aldehydes. In particular, it is suitable for the manufacture of ethyl acetate, which is significant in the industry.

The invention claimed is:

1. A Cu—ZnO—Al$_2$O$_3$—ZrO$_2$ catalyst for ester production, which comprises:
    per mole of copper, 0.05–1 mole of zinc oxide, 0.1–1 mole of aluminum oxide and 0.1–1 mole of zirconium oxide, the catalyst having been obtained by reducing with hydrogen, a calcined form of a precipitate prepared by the reaction of a copper salt, a zinc salt, an aluminum salt and a zirconium salt with an alkali metal hydroxide.

2. A process of preparing Cu—ZnO—Al$_2$O$_3$—ZrO$_2$ catalyst for ester production, which comprises:
    reducing with hydrogen a calcined form of a precipitate prepared from an aqueous solution of copper nitrate, zinc nitrate, aluminum nitrate and zirconyl nitrate, and an alkali metal hydroxide, wherein the mixed aqueous solution contains 0.05–1 mole of zinc nitrate, 0.2–2 moles of aluminum nitrate, 0.1–1 moles of zirconium nitrate, per mole of copper nitrate, the catalyst comprising per mole of copper, 0.05–1 mole of zinc oxide, 0.1–1 mole of aluminum oxide and 0.1–1 mole of zirconium oxide.

3. A process for producing an ester, comprising bringing an alcohol into contact with a catalyst as claimed in claim 1 in a vapor phase, and dehydrogenating the alcohol to form an ester.

4. The process for producing an ester as claimed in claim 3, wherein the alcohol is an alcohol having 1–4 carbon atoms.

5. The process for producing an ester as claimed in claim 3, wherein ethyl acetate is produced from ethyl alcohol.

6. A process for producing an ester, comprising bringing an alcohol and an aldehyde into contact with a catalyst as claimed in claim 1 in a vapor phase to form an ester.

7. The process for producing an ester as claimed in claim 6, wherein the alcohol and the aldehyde are an alcohol and an aldehyde having 1–4 carbon atoms.

8. The process for producing an ester as claimed in claim 6, wherein ethyl acetate is produced from ethyl alcohol and acetaldehyde.

9. The process for producing an ester as claimed in claim 6, wherein butyl acetate is produced from butyl alcohol and acetaldehyde.

* * * * *